United States Patent
Slusarz, Jr.

(10) Patent No.: US 10,575,980 B2
(45) Date of Patent: *Mar. 3, 2020

(54) BOOT WITH LOCKABLE STRAP

(71) Applicant: Smith & Nephew, Inc., Memphis, TN (US)

(72) Inventor: John Albert Slusarz, Jr., Hopedale, MA (US)

(73) Assignee: Smith & Nephew, Inc., Memphis, TN (US)

( * ) Notice: Subject to any disclaimer, the term of this patent is extended or adjusted under 35 U.S.C. 154(b) by 479 days.

This patent is subject to a terminal disclaimer.

(21) Appl. No.: 15/348,520

(22) Filed: Nov. 10, 2016

(65) Prior Publication Data

US 2017/0056234 A1    Mar. 2, 2017

Related U.S. Application Data

(63) Continuation of application No. 14/597,594, filed on Jan. 15, 2015, now Pat. No. 9,510,970, which is a
(Continued)

(51) Int. Cl.
*A61F 5/37* (2006.01)
*A61F 5/01* (2006.01)
(Continued)

(52) U.S. Cl.
CPC .......... *A61F 5/3769* (2013.01); *A61B 5/0555* (2013.01); *A61F 5/0116* (2013.01);
(Continued)

(58) Field of Classification Search
CPC .... A61F 5/0111; A61F 5/0127; A61F 5/3761; A61F 5/3769; A61G 13/125; A43C 7/08; A43C 11/14; A43B 5/04
(Continued)

(56) References Cited

U.S. PATENT DOCUMENTS 2,442,266 A    5/1948  Davis
2,665,431 A    1/1954  Elsner
(Continued)

FOREIGN PATENT DOCUMENTS

EP           2529719 A1   12/2012
WO     WO2007021806 A1    2/2007
WO     WO2009059434 A1    5/2009

OTHER PUBLICATIONS

Trail Hiking Snowshoes for Women—Silver 9 by Crescent Moon, reprinted from http://crescentmoonsnowshoes.com/womens/silver9.php, (accessed Aug. 28, 2013).
(Continued)

*Primary Examiner* — Keri J Nelson
(74) *Attorney, Agent, or Firm* — Fish & Richardson P.C.

(57) ABSTRACT

In some implementations, a boot includes an outer shell having a first side and a second side located opposite the first side. The boot may include a retention strap. The boot may include a first one-way tensioning device coupled to the first side of the outer shell, where the first one-way tensioning device is configured to allow movement of the retention strap in a first direction and to restrain movement of the retention strap opposite the first direction. The boot may include a second one-way tensioning device coupled to the second side of the outer shell, where the second one-way tensioning device is configured to allow movement of the retention strap in a second direction and to restrain movement of the retention strap opposite the second direction.

19 Claims, 10 Drawing Sheets

Related U.S. Application Data continuation of application No. 14/012,238, filed on Aug. 28, 2013, now Pat. No. 8,944,065.

(60) Provisional application No. 61/804,331, filed on Mar. 22, 2013.

(51) Int. Cl.
*A61G 13/12* (2006.01)
*A61B 5/055* (2006.01)

(52) U.S. Cl.
CPC .............. *A61F 5/37* (2013.01); *A61G 13/123* (2013.01); *A61G 13/1245* (2013.01)

(58) Field of Classification Search
USPC ........ 602/27; 128/882, 845; 36/117.1–119.1, 36/122–125
See application file for complete search history.

(56) References Cited

U.S. PATENT DOCUMENTS

| | | | |
|---|---|---|---|
| 4,407,277 A | 10/1983 | Ellison | |
| 4,788,780 A * | 12/1988 | Boggs | A43B 3/16 36/117.2 |
| 5,370,133 A | 12/1994 | Darby et al. | |
| 5,645,079 A | 7/1997 | Zahiri et al. | |
| 6,526,629 B1 | 3/2003 | Warner et al. | |
| 6,722,060 B2 * | 4/2004 | Okajima | A63C 10/10 36/115 |
| 7,018,352 B2 | 3/2006 | Pressman et al. | |
| 7,281,341 B2 | 10/2007 | Reagan et al. | |
| 7,832,401 B2 | 11/2010 | Torrie et al. | |
| 7,947,006 B2 | 5/2011 | Torrie et al. | |
| 8,944,065 B2 * | 2/2015 | Slusarz, Jr. | A61B 5/0555 128/845 |
| 9,510,970 B2 * | 12/2016 | Slusarz, Jr. | A61B 5/0555 |
| 2004/0133979 A1 | 7/2004 | Newkirk et al. | |
| 2008/0150259 A1 * | 6/2008 | Veyrat-Charvillon | A63C 10/06 280/623 |
| 2009/0134602 A1 | 5/2009 | Pontano et al. | |
| 2011/0009791 A1 | 1/2011 | Hopmann | |
| 2011/0030244 A1 | 2/2011 | Motawi et al. | |
| 2012/0259261 A1 | 10/2012 | Clark et al. | |
| 2012/0305005 A1 | 12/2012 | Keith-Lucas et al. | |
| 2012/0305006 A1 | 12/2012 | Keith-Lucas et al. | |

OTHER PUBLICATIONS

"Allen® Traction Boot," reprinted from http://www.allenmedical.com/product/orthopaedics-products/A-93000.html, accessed Aug. 28, 2013.

"Stainless Steel Cam Buckle 1 in.," reprinted from http://www.strapworks.com/Stainless_Steel_Cam_Buckle_p/sscb1.htm (accessed Aug. 28, 2013).

International Search Report and Written Opinion for International Application No. PCT/US2014/030999, dated Jul. 10, 2014.

"Allen® Traction Boot," http://www.allenmedical.com/product/orthopaedics-roducts/A-93000.html, copyright 2011, Archive of web page dated Nov. 26, 2011, retrieved from https://web.archive.org/web/20111126175917/http://www.allenmedical.com/product/orthopaedics-products/A-93000.html#tabs-2 (8 pages).

Notice of Reasons for Rejection in Japanese Application No. 2016-504331.

Examination Report No. 1 for Australian Application No. 2014236064.

\* cited by examiner

FIG. 9

BOOT WITH LOCKABLE STRAP

CROSS-REFERENCE TO RELATED APPLICATION

This application is a continuation of U.S. patent application Ser. No. 14/597,594, filed Jan. 15, 2015, now allowed, which is a continuation of U.S. patent application Ser. No. 14/012,238, filed Aug. 28, 2013, now U.S. Pat. No. 8,944,065, issued Feb. 3, 2015, which claims priority from U.S. Provisional Application Ser. No. 61/804,331, filed Mar. 22, 2013. The prior applications are incorporated herein by reference in their entirety.

TECHNICAL FIELD

This document relates to boots with lockable straps.

BACKGROUND

To gain access to a hip joint to perform hip arthroscopy or another procedure, the femoral head (ball) of the hip joint may be dislocated from the acetabulum (socket) using traction. A hip distractor system for applying traction can be attached to an operating table and can be used to dislocate a hip joint or otherwise position the patient. A hip distractor system can include a boot that attaches to a patient's foot to allow traction on the leg.

SUMMARY

In a general aspect, a method includes placing a patient's foot in a boot that includes a cam buckle, a pad, and a retention strap. The method includes placing the retention strap over the top of the foot. The method includes arranging the pad relative to the top of the foot. The method includes pressing on the pad to position the foot within the boot, and while pressing on the pad, applying tension on the retention strap to advance the retention strap through the cam buckle, the cam buckle being configured to automatically limit movement of the retention strap through the cam buckle when tension on the retention strap is released. The method includes reducing tension on the retention strap to cause the cam buckle to limit movement of the retention strap through the cam buckle.

Implementations may include one or more of the following aspects. For example, applying tension on the retention strap to advance the retention strap through the cam buckle includes applying tension on a first end of the retention strap to advance a first portion of the retention strap through a first cam buckle; and the method further includes, while pressing on the pad, applying tension on a second end of the retention strap to advance a second portion of the retention strap through a second cam buckle configured to automatically limit movement of the retention strap through the second cam buckle tension on the retention strap is released. Applying tension on the retention strap to advance the retention strap through the cam buckle includes applying tension on the retention strap to advance the retention strap through a cam buckle that allows infinite adjustability of the retention strap relative to the cam buckle by securing the position of the retention strap with respect to the cam buckle at any position along a continuous length of the retention strap. Applying tension on the retention strap to advance the retention strap through a cam buckle includes applying tension on the retention strap that simultaneously tightens a heel retention strap that extends along a heel of the foot and is looped around the retention strap.

Implementations may include one or more of the following aspects. For example, pressing on the pad to position the foot within the boot includes pressing against the foot in a generally inferior direction; and applying tension on the retention strap includes applying tension on the retention strap by pulling an end of the retention strap in a generally superior direction. Pressing against the foot in a generally inferior direction includes placing a hand over the pad and pressing the pad with the hand toward a sole of the boot. Arranging the pad relative to the top of the foot includes arranging a pad that is adjustably coupled to the retention strap and located between the retention strap and the top of the foot, and placing the retention strap over the top of the foot includes clasping a buckle of the retention strap, the buckle being located over the pad. The method further includes, after applying tension to the retention strap: tightening a toe strap located over toes of the foot; and tightening a leg strap around a leg to which the foot is attached. The method further includes, before placing the patient's foot in the boot, placing the patient's foot in a padded liner. Placing the patient's foot in the boot includes placing the patient's foot and the padded liner within the boot, and pressing on the pad to position the foot within the boot includes compressing the pad or the padded liner against the foot. The method further includes attaching the boot to a hip distraction system, and applying traction to the patient's leg by applying a force to the boot using the hip distraction system. The method further includes dislocating a hip of the patient by applying a force to the boot with the hip distraction system.

In another general aspect, a boot includes an outer shell, a retention strap, a pad coupled to the retention strap, and a cam buckle coupled to the outer shell. The retention strap extends through the cam buckle. The cam buckle is configured to permit the retention strap to advance through the cam buckle when tension is applied to the retention strap and to automatically limit movement of the retention strap through the cam buckle when tension on the retention strap is released.

Implementations may include one or more of the following features. For example, the cam buckle is a first cam buckle, and the boot further includes a second cam buckle coupled to the outer shell, the retention strap extending through the second cam buckle, the second cam buckle being configured to permit the retention strap to advance through the second cam buckle when tension is applied to the retention strap and automatically impede movement of the retention strap through the second cam buckle when tension on the retention strap is released. The outer shell has a first exterior lateral surface and a second exterior lateral surface that faces opposite the first exterior lateral surface, and the first cam buckle is attached to the first exterior lateral surface and the second cam buckle is attached to the second exterior lateral surface. The pad includes an extension configured to extend around the retention strap to capture the pad about the retention strap and allow the pad to be movable along the length of the retention strap when the pad is captured about the retention strap. The retention strap includes a first handle that includes a first loop of the retention strap and a second handle that includes a second loop of the retention strap. The retention strap includes a first portion and a second portion that is detachable from the first portion, and the retention strap includes a buckle configured to attach the first portion and the second portion.

Implementations may include one or more of the following aspects. For example, the boot further includes: a heel strap having a first portion and a second portion, the first portion of the heel strap being looped around the first portion of the retention strap and the second portion of the heel strap being looped around the second portion of the retention strap; and a heel pad attached to the heel strap, the heel pad being located to cushion a heel of the patient when a foot of the patient is located in the boot, where the heel strap is configured such that advancing the retention strap through the cam buckle tightens the heel strap. The boot further includes: a calf pad positioned at an interior of the outer shell, the calf pad extending in a superior-inferior direction and being located to cushion a back side of a leg of a patient when a foot of the patient is located in the boot; a leg strap attached to the outer shell, the leg strap being located to extend at least partially around the calf pad and the leg of a patient when the foot of the patient is located in the boot; and a shin pad connected to the leg strap, the shin pad being located to extend between the leg strap and a front side of the leg of the patient when the foot of the patient is located in the boot. The boot further includes: a sole pad positioned at the interior of the outer shell, the sole pad extending in an anterior-posterior direction and being located to cushion a bottom side of the foot of the patient when the a foot of the patient is located in the boot; a toe strap attached to the outer shell, the toe strap being located to extend at least partially around the sole pad and a top side of the foot when the foot is located in the boot; and a toe pad connected to the toe strap, the toe pad being located to extend between the toe strap and the top side of the foot when the foot is located in the boot. The cam buckle comprises a cam and teeth configured to engage the retention strap, the cam buckle being configured to move the teeth toward the cam when tension on the retention strap is released. The outer shell has opposing lateral walls and defines an opening in each of the lateral walls, and the cam buckles are mounted to the lateral walls at the openings such that the retention strap extends from between the lateral walls through the openings into the cam buckles.

The details of one or more implementations are set forth in the accompanying drawings and the description below. Other features, objects, and advantages will be apparent from the description and drawings, and from the claims.

DETAILED DESCRIPTION

Figure 1:
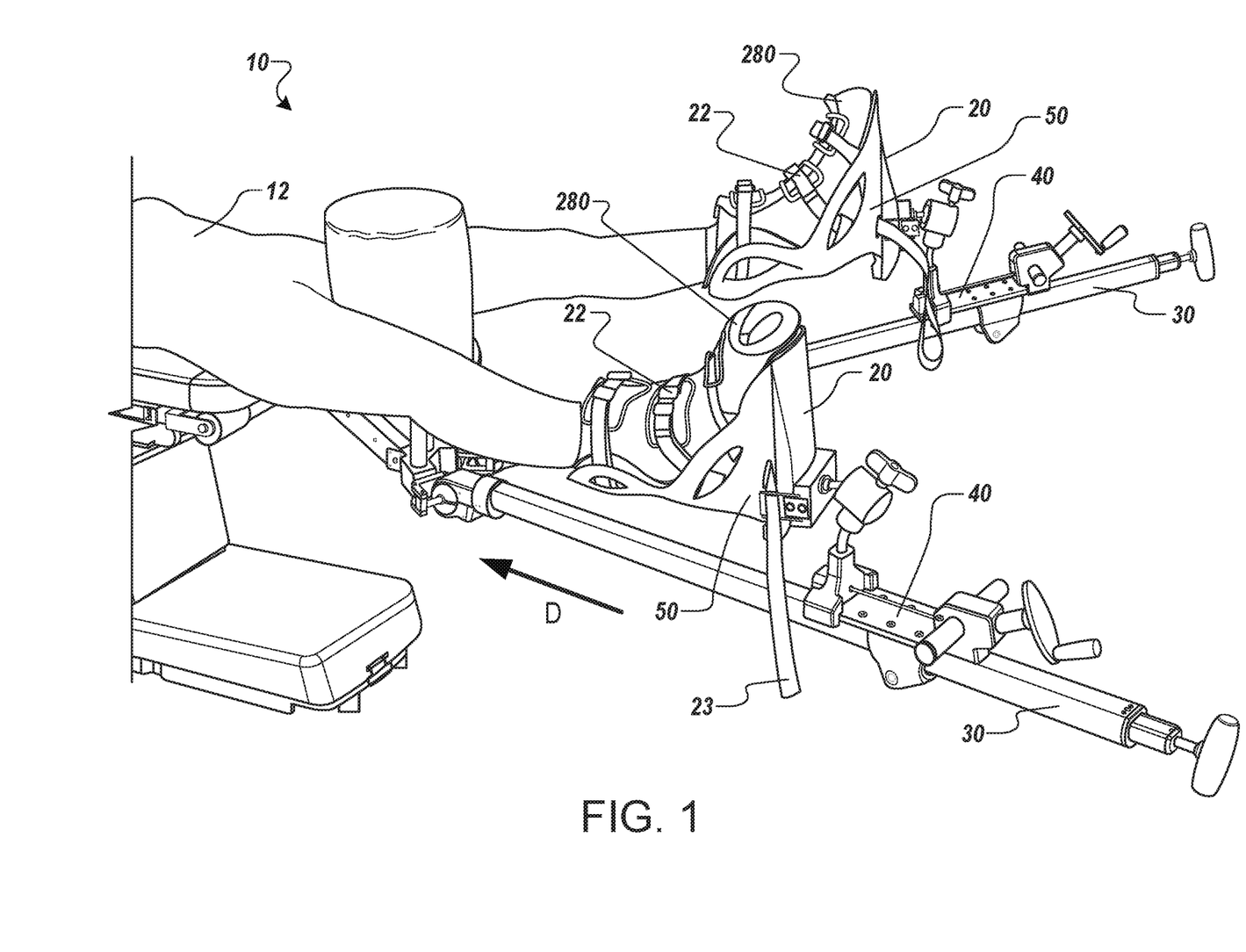
FIG. 1 is a perspective view of a hip distraction system.
Figure 2:
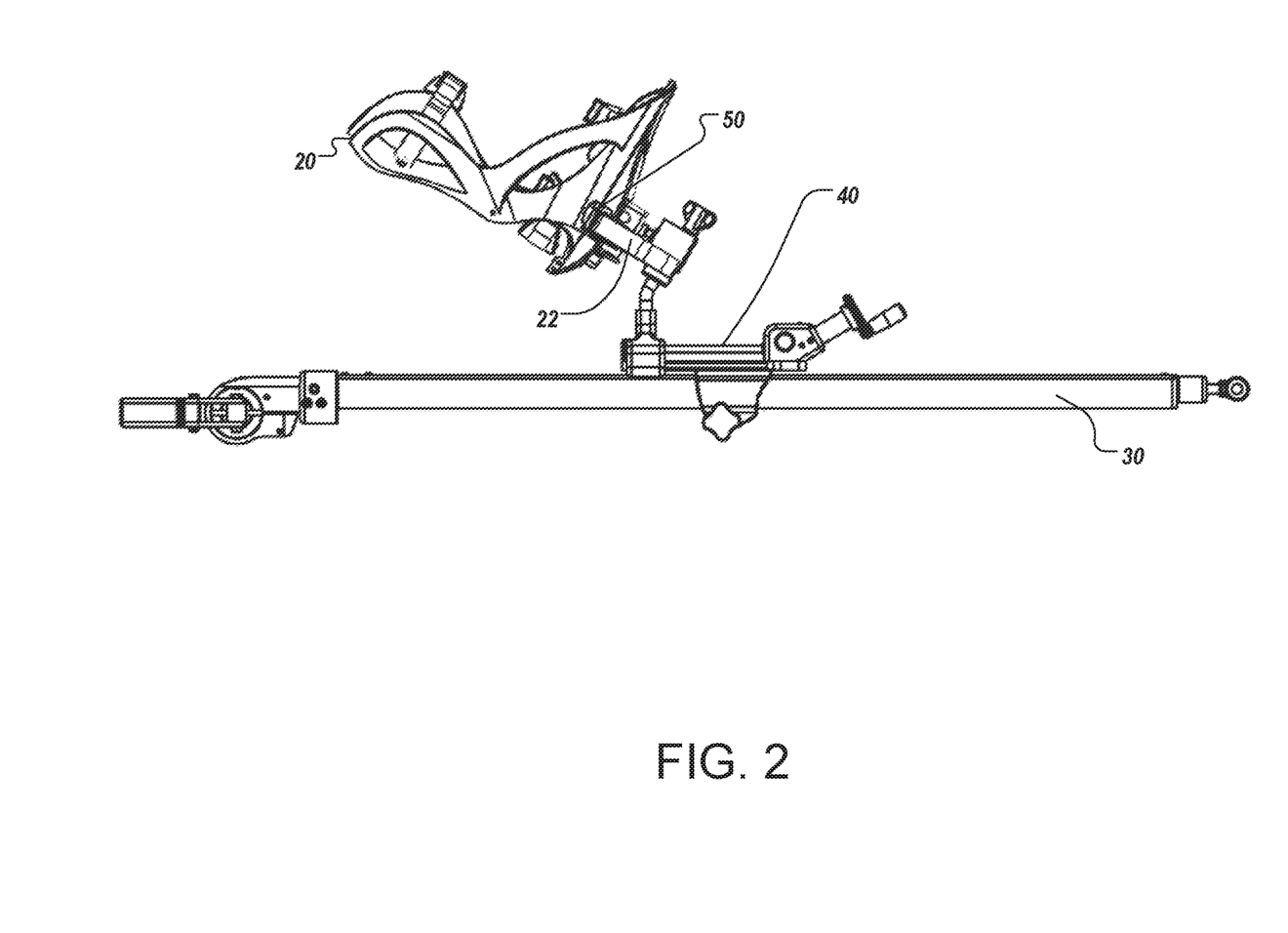
FIG. 2 is a side view of a portion of the hip distraction system.

Referring to FIGS. 1 and 2, a hip distraction system 10 can be used to position a patient 12 for surgery. The hip distraction system 10 can include boots 20 that can be secured to the patient's feet. Each boot 20 includes a retention strap 22 that extends over the top of the patient's foot and through cam buckles 50, or another one-way tensioning device located at opposite sides of the boot 20. To tighten the retention strap 22, a surgeon can apply tension to the retention strap 22 to advance the retention strap 22 through one of the cam buckles 50. For example, the surgeon may pull an end of the retention strap 22 in a generally superior direction. In the example of FIG. 1, the end 23 of the retention strap 22 may be pulled in the direction of arrow D (e.g., generally parallel to the distractor mast 30 and away from the sole of the boot 20) to tighten the retention strap 22 over the foot. When the desired position of the retention strap 22 is achieved, the surgeon releases tension on the retention strap 22 and the cam buckles 50 automatically hold the retention strap 22 in position. In this manner, the surgeon may secure the position of the retention strap 22 by releasing or reducing tension on the retention strap 22, without any further action to engage a locking mechanism. Each cam buckle 50 is configured to hold the retention strap 22 at any position along a continuous region of the retention strap 22. As a result, the surgeon is not limited to a finite number of discrete locking positions of the strap relative to the cam buckle 50. After tightening one side of the retention strap 22, the surgeon may apply tension to the other end of the retention strap 22, advancing the retention strap 22 through the other cam buckle 50 to a desired position and releasing the strap to secure the other cam buckle.

The hip distraction system 10 includes, for each leg of the patient 12, a boot 20, a distractor mast 30, and a sliding carriage 40. After the patient's feet are secured in the boots 20, the boots 20 can be attached to the sliding carriages 40. The sliding carriages 40 may be moved along the distractor mast 30 to apply tension to the patient's legs. If appropriate for a surgical procedure, the hip distraction system 10 can be used to dislocate the patient's hip joint and maintain appropriate distraction during the procedure.

Referring to FIGS. 3A-5, the boot 20 includes an outer shell 100 that defines the general shape of the boot 20 and provides a framework to which the other components of the boot 20 are attached. The boot 20 also includes a leg strap 110, a heel strap 120, and a toe strap 130, in addition to the retention strap 22 that extends through the cam buckles 50. The boot also includes a sole pad 140, a calf pad 150, a shin pad 160, a heel pad 170 (see FIG. 5), a toe pad 180, and a bridge pad 190.

Figure 3A:
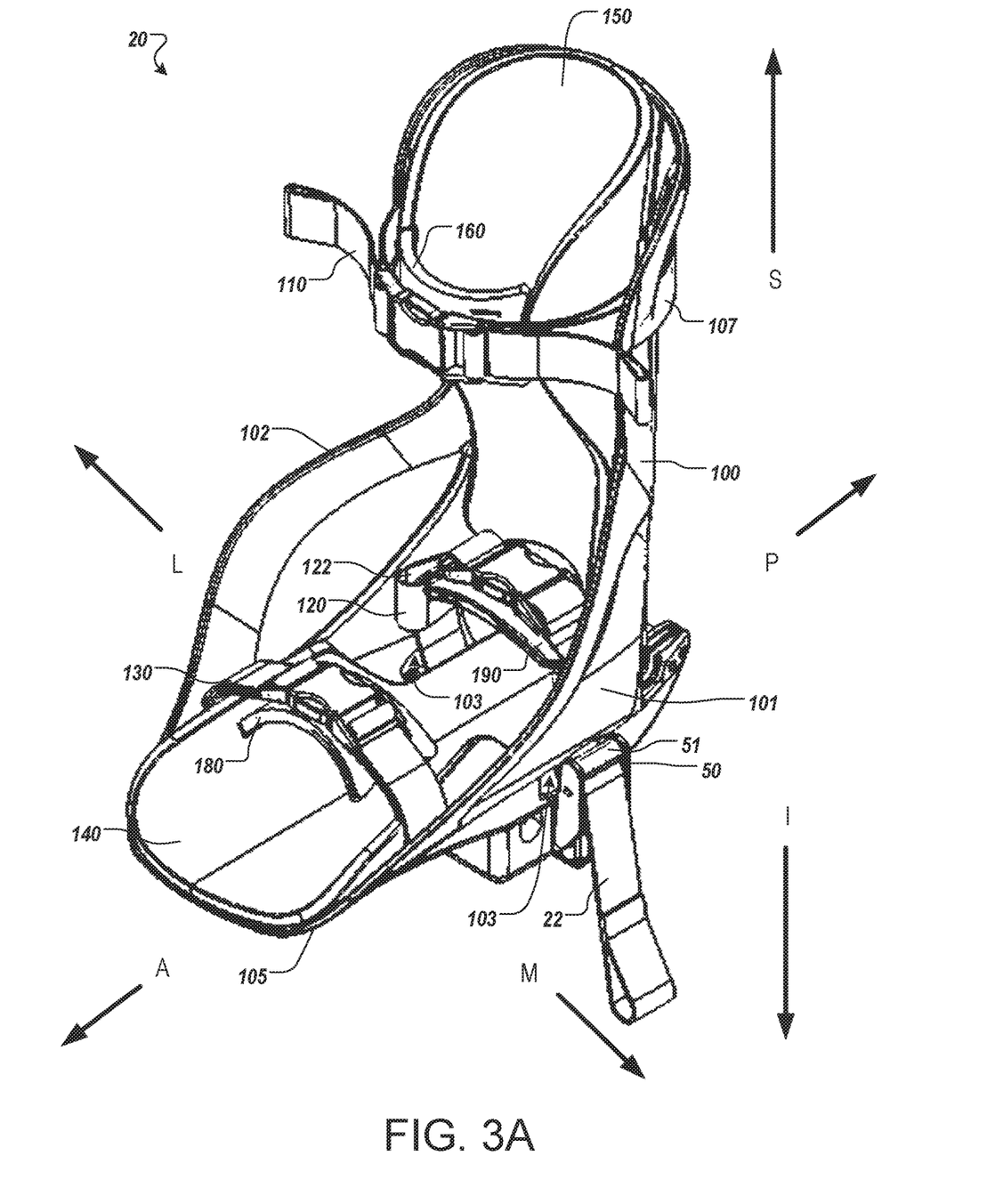
FIG. 3A is a perspective view of a boot.

The boot 20 may be used with either a right foot or a left foot. When a right foot is placed in the boot 20, anatomical directions (e.g., superior, inferior, medial, lateral, anterior, and posterior) illustrated show the position of the boot 20 relative to the foot. If a left foot is placed in the boot 20, the medial and lateral directions shown would be reversed. Medial and lateral sides of the boot 20 are both referred to generally below as "lateral sides," since the medial and lateral orientation will vary depending on which foot is placed in the boot.

The outer shell 100 of the boot 20 has opposing lateral sides 101, 102. The cam buckles 50 are mounted to the exterior of the outer shell 100, with one cam buckle 50 at each of the lateral sides 101, 102. The outer shell 100 defines an opening 103 in each of the lateral sides 101, 102, and the cam buckles 50 are located at the openings 103. As a result, the retention strap 22 can extend from the interior of the boot 20 through the cam buckles 50 by passing through the openings 103 in the outer shell 100. The openings 103 can be located so that the retention strap 22 exits the outer shell 100 at a position generally at or below the sole pad 140.

Figure 3B:
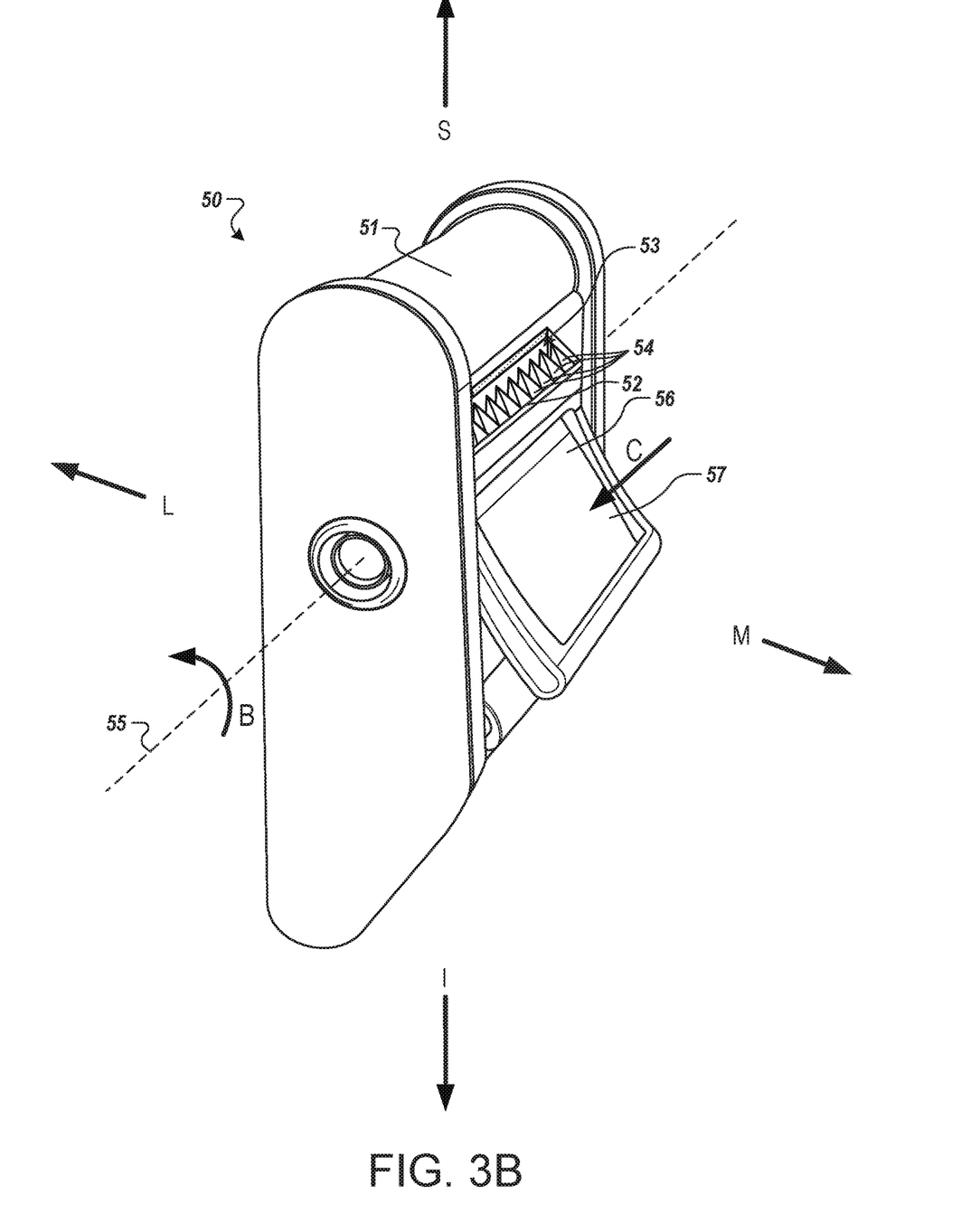
FIG. 3B is a perspective view of a cam buckle of the boot.

The retention strap 22 is positioned to extend over the top of the foot, generally over the bridge or instep of the foot. The retention strap 22 can apply traction to the heel area of the foot, for example, by pressing inferiorly and posteriorly on the top of the foot when the retention strap 22 is tightened. The position of the retention strap 22 is infinitely adjustable relative to the cam buckles 50. Each cam buckle 50 is configured to secure the strap at any position along the length of the retention strap 22 that passes through the cam buckle 50. As a result, the surgeon may secure the retention strap 22 at a desired position along the length of the retention strap 22 without having to select from among discrete positions of the strap relative to the cam buckle 50. Referring to FIG. 3B, an example of a cam buckle 50 is shown. One example of a cam buckle that may be used with the boot 20 is part number MCB1, provided by Strapworks.com. The MCB1 cam buckle is a metal cam buckle designed to accept 1" nylon strapping. In some implementations, the cam buckle 50 selected for the boot can be a cam buckle with a load rating of at least 60 pounds of force, or at least 100 pounds of force, or more. In some implementations, the cam buckle 50 may be designed to operate with applied forces of at least 250 pounds, at least 500 pounds, at least 750 pounds, or more.

Each cam buckle 50 of the boot 20 includes a cam 51 located opposite a gripping portion 52. The cam buckle 50 defines a gap 53 between the cam 51 and gripping portion 52, and the retention strap 22 extends through the gap 53. In the example shown, the gripping portion 52 includes teeth 54 that engage the retention strap 22 to limit motion of the retention strap 22 through the cam buckle 50. Surfaces with other contours, flat surfaces, textured surfaces, and other types of gripping portions 52 may additionally or alternatively be used.

The cam buckle 50 includes a spring or other resilient member configured to exert pressure between the cam 51 and the gripping portion 52 to secure the position of the retention strap 22, but which also permits movement of the cam 51 and/or gripping portion 52 to allow the retention strap 22 to advance when a force is applied on the retention strap 22. The cam buckle 50 may be configured so that the gripping portion 52 moves relative to a stationary cam 51, or that the cam 51 moves relative to a stationary gripping portion 52.

In the illustrated example, the gripping portion 52 is formed on a portion 56 of the cam buckle 50 that moves relative to the cam 51 by rotating about an axis 55. The portion 56 includes a release lever 57 that a surgeon may press to rotate portion 56 about the axis 55 to release the retention strap 22. A spring or other biasing member in the cam buckle 50 exerts a force that tends to rotate the portion 56 in the direction of arrow B, to the position shown which can lock the position of the retention strap within the cam buckle 50.

When tension is applied to the end of the retention strap 22, for example, by a surgeon pulling an end of the retention strap 22, the force on the retention strap 22 can rotate the portion 56 slightly about the axis 55 in a direction opposite arrow B. This rotation moves the gripping portion 52 (e.g., in a generally medial direction in the illustration) and expands the gap 53. This motion can alter the forces exerted on the retention strap 22 between the gripping portion 52 and the cam 51 enough to permit the retention strap 22 to advance through the cam buckle 50 between the cam 51 and the gripping portion 52. The cam 51 also redirects force on the retention strap 22 so that tension applied in, for example, a superior direction or a medial direction, results in the central portion of the retention strap 22 pressing inferiorly (and in some instances inferiorly and posteriorly) on the top of the foot.

The cam buckle 50 can be of a type that does not require a button or other mechanism to be manually manipulated by the surgeon to permit advancement of the retention strap 22 (e.g., pulling the retention strap 22 out of the boot 20 through the cam buckle to tighten the retention strap 22 over the foot). As a result, in some implementations, the surgeon may tighten the retention strap 22 simply by pulling the retention strap 22 through the cam buckle. In other implementations, a cam buckle 50 may optionally include a switch or other mechanism that may be set to permit or disallow advancement of the retention strap 22.

When tension on the retention strap 22 is released, for example, by a surgeon reducing tension on or letting go of an end of the retention strap 22, the biasing force on the cam 51 moves the gripping portion 52 toward the cam 51, reducing the size of the gap 53 and pressing the retention strap 22 into the gripping portion 52 to secure the position of the retention strap 22 relative to the cam buckle 50. The cam buckle 50 may impede the retention strap 22 from receding through the cam buckle 50, e.g., to prevent backward motion in a direction opposite the direction that the retention strap 22 was advanced. By maintaining the position of the retention strap 22 relative to the cam buckle 50, the cam buckle 50 limits loosening of the retention strap 22 on the foot after tension is released.

To release the retention strap 22, a surgeon can press the release lever 57 of the cam buckle 50, for example, in the direction of arrow C. This pressure can counteract the biasing force of the cam member to rotate the portion 56, expanding the gap 53 and disengaging the gripping portion 52 from the retention strap 22. The release lever 57 can project from the cam buckle 50 for ease of access by a surgeon. For example, in the example illustrated, the release lever 57 extends medially and inferiorly from the medial side of the cam buckle. This arrangement may suggest to the surgeon that pressing the release lever 57 to align the release lever 57 with the medial side will release the locking mechanism of the cam buckle 50.

The cam buckles 50 may operate using a mechanism different from the interactions described above. For example, the cam buckles 50 may each include a ratchet and pawl or another one-way tensioning mechanism that permits advancement of the retention strap 22 when tension is applied and automatically secures the position of the retention strap 22 when tension is released. As another example, one of the cam 51 and the gripping portion 52 may be configured to translate along an axis, in addition to or instead of rotating about an axis, to expand or close the gap 53.

The cam buckle 50 may be configured to automatically limit movement of the retention strap when tension on the retention strap 22 is released. For example, the act of reducing or releasing tension may alone cause the cam buckle 50 to hold the position of the retention strap 22. The cam buckle 50 may act to lock the retention strap 22 in place without any other action by the user. As an example, when tension on the retention strap 22 is reduced, the biasing force of the cam buckle 50 can cause the cam 51 to move toward the gripping portion of the cam buckle 50, securing the position of the retention strap 22 without any user manipulation of the cam buckle 50 or any secondary locking mechanism. In some implementations, after the retention strap 22 has been advanced to a desired position, no user intervention is required to lock the retention strap 22 in place other than reducing or releasing tension on the retention strap 22, either while tension is reduced or subsequent to releasing tension.

Referring again to FIG. 3A, the leg strap 110, the heel strap 120, and the toe strap 130 also help secure a foot within the boot 20. The heel strap 120 is located at the posterior of the boot 20 and extends across the back of the patient's foot at or slightly above the heel. The heel strap 120 extends generally perpendicular to the retention strap 22. The heel strap 120 is connected to the retention strap 22 so that tightening the retention strap 22 over the top of the foot also tightens the heel strap 120 against the heel. The heel strap 120 has two ends that each form a loop 122. The retention strap 22 passes through each of the loops 122. When the retention strap 22 is tightened, the loops 122 are pulled toward each other (e.g., toward each other along the medial-lateral axis) and the heel strap 120 is pulled in an anterior direction. As a result, the heel strap is configured so that advancing the retention strap 22 through the cam buckle 50 tightens the heel strap 120 against the patient's foot. The heel strap 120 is not directly connected to the outer shell 100. Movement of the heel strap 120 relative to the rest of the boot 20 is only limited by the loops 122 that extend around the retention strap 22 to capture the heel strap 120.

In some implementations, the heel strap 120 helps balance the forces exerted on the retention strap 22 and helps align the retention strap 22 with the cam buckle 50. When the patient's foot is placed in the boot 20 with the retention strap 22 over the top of the foot, the patient's ankle may cause the retention strap 22 to be located anterior to the cam buckle 50.

When the retention strap 22 is tightened, the patient's ankle exerts an anterior force on the retention strap 22, which is out of alignment with the cam buckle 50. The heel strap 120 engages the patient's heel and pulls posteriorly on the portions of the retention strap 22 passing through the loops 122, which can align the retention strap 22 with the cam buckle 50 by counteracting some or all of the anterior force exerted on the retention strap 22 by the top of the patient's foot.

The toe strap 130 extends over the top of the patient's foot, generally over the toes of the foot. The toe pad 180 is positioned under the toe strap 130, so that the toe pad 180 extends between the toe strap 130 and the toes when a foot is placed in the boot 20. The toe pad 180 may be formed of polyester foam or another padding material, and the toe pad 180 is attached to the toe strap 130 by, for example, Velcro, stitching, adhesive, or another fastener.

The outer shell 100 has a base 105, and the sole pad 140 extends along the interior of the base 105. The sole pad 140 is fastened to the base 105 with, for example, Velcro, adhesive, or another fastener. When a patient's foot is secured in the boot, the sole pad 140 cushions the sole of the patient's foot as it is pressed toward the base 105. Medial and lateral sides of the sole pad 140 curve superiorly to cushion sides of the foot. The toe strap 130 extends at least partially around the sole pad 140. The toe strap 130 extends between the outer shell 100 and the sole pad 140 so portions of the sole pad 140 are enclosed within the toe strap 130. When the toe strap 130 is tightened around the foot, the toe strap 130 can press the sides of the sole pad 140 against medial and lateral sides of the foot in addition to pressing the foot inferiorly toward the sole pad 140.

Figure 4:
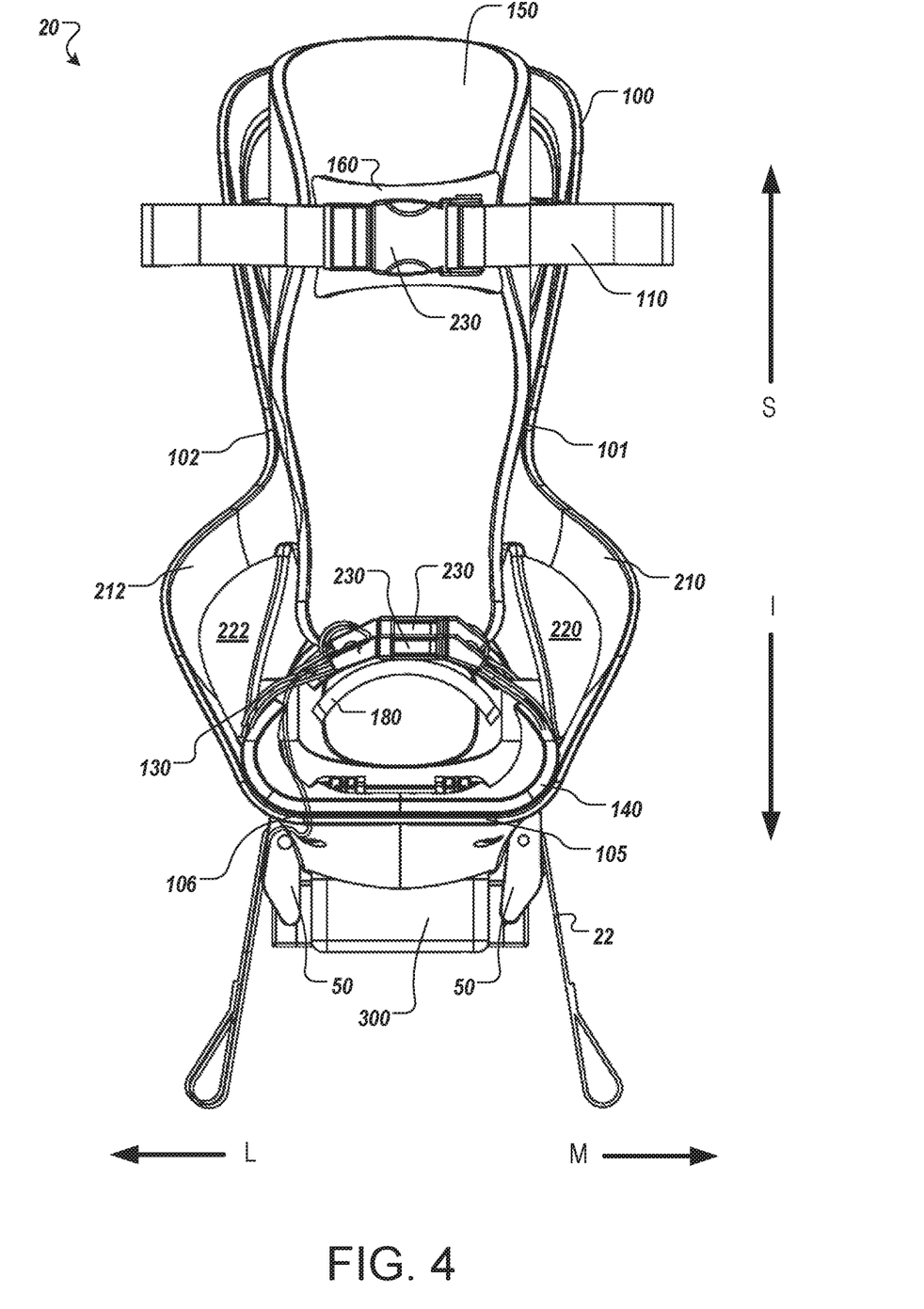
FIG. 4 is a front view of the boot.

The base 105 of the outer shell 100 can include, at the interior of the outer shell 100, an upper surface 106 that the sole pad 140 rests against (see FIG. 4). The openings 103 in the lateral sides 101, 102 can extend through the upper surface 106 along the superior-inferior axis, permitting the retention strap 22 to extend inferiorly through the upper surface 106. The retention strap 22 can extend inferiorly through the upper surface 106 before exiting the openings 103 and into the cam buckles 50. As a result, the retention strap 22 engages the cams 51 of the cam buckles 50 inferior to the sole pad 140 and the upper surface 106, which can facilitate tightening of the retention strap 22.

The leg strap 110 extends over the front of the patient's leg when the patient's foot is in the boot 20. The shin pad 160 is positioned under the leg strap 110 so the shin pad 160 extends between the leg strap and a front side of the patient's leg. The shin pad 160 may be formed of polyester foam or another padding material, and the shin pad 160 is attached to the leg strap 110 by, for example, Velcro, stitching, adhesive, or another fastener.

The leg strap 110 is attached to the outer shell 100 so that tightening the leg strap 110 presses the leg posteriorly toward the back of the boot 20. The calf pad 150 is attached to the interior of the outer shell 100 and is located to cushion the back side of the patient's leg. The calf pad 150 extends in a superior-inferior direction, and also curves anteriorly at medial and lateral edges to extend partially around the patient's leg. The calf pad 150 is fastened to the interior of the outer shell 100 with, for example, Velcro, adhesive, or another fastener. The leg strap 110 extends between the interior of the outer shell 100 and the calf pad 150, so that tightening the leg strap 110 presses the calf pad 150 against medial and lateral sides of the patient's foot as well as pressing the leg posteriorly toward the calf pad 150.

Figure 5:
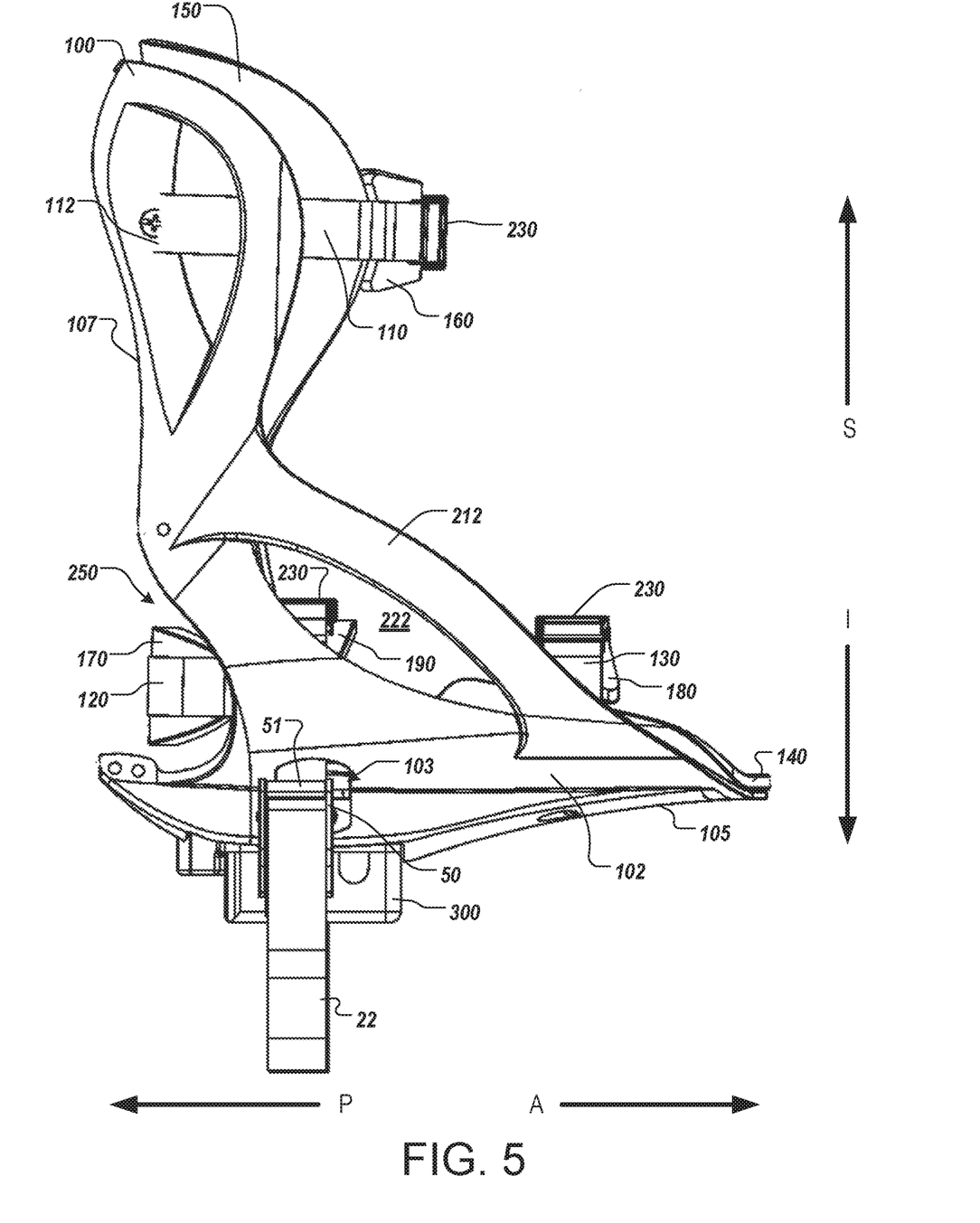
FIG. 5 is a side view of the boot.

Referring to FIGS. 4 and 5, the outer shell 100 has a leg portion 107 that extends generally in a superior-inferior direction, perpendicular to the base 105 of the outer shell 100. Curved extensions 210, 212 extend between the leg portion 107 and the base 105 on lateral sides 101, 102 of the boot 20. The extension 210 curves medially outward from the leg portion 107 and then curves laterally to join the base 105. The extension 212 curves laterally outward from the leg portion 107 and then curves medially to join the base 105. The outer shell 100 defines openings 220, 222 adjacent the extensions 210, 212.

The front of the outer shell 100 is open to facilitate placement of the foot within the boot 20. For example, the outer shell 100 is open facing in an anterior direction and also in a superior direction. The outer shell 100 does not cover a patient's toes or extend over the top of the foot or leg when the foot is placed in the boot 20.

The placement of the extensions 210, 212 and openings 220, 222 permits a surgeon to place his fingers through the opening 220, 220 to grasp the extensions 210, 212. The surgeon may use the extensions 210, 212 as handles to position the boot 20 with respect to the patient's foot.

As shown in FIGS. 3-5, the retention strap 22, the toe strap 130, and the leg strap 110 can each include two portions that are joined by a buckle 230 or other fastener. For example, the buckles 230 can be side release buckles (e.g., flat squeeze release buckles) located at the center of the straps 22, 130, 110. The surgeon can engage the ends of a buckle 230 to connect a strap 22, 130, 110 around the patient's foot or leg, and the surgeon can the separate the ends of the buckle 230 remove the foot from the boot 20. The shin pad 160, the toe pad 180, and the bridge pad 190 are each located under one of the buckles 230 to cushion the patient's foot or leg in the area of the buckles 230.

The leg strap 110 has ends that are attached to the leg portion 107 of the outer shell 100. For example, each end of the leg strap 110 can be secured to the leg portion 107 with a screw or other fastener at an attachment point 112. The toe strap 130 has ends that are attached to the base 105 of the outer shell 100. For example, each end of the toe strap 130 can be secured to the base 105 with a screw or other fastener at the interior of the outer shell 100, under the sole pad 140. From their respective points of attachment to the outer shell 100, the portions of the leg strap 110 and the toe strap 130 that extend around the patient's leg and foot can be located entirely between the lateral sides 101, 102 of the outer shell 100. The straps 110, 130 can be tightened by adjusting the position of the straps 110, 130 relative to the corresponding buckles 230. Because the straps 110, 130 are located within the interior of the outer shell 100, tightening the straps 110, 130 does not require any advancement of the straps 110, 130 through or around the outer shell 100. In addition, because the straps 110, 130 do not capture or extend around any exterior portions of the outer shell 100, the straps 110, 130 may be tightened without resistance from the outer shell 100. The portion of the retention strap 22 located between the openings 103 is also located entirely between the lateral sides 101, 102 of the outer shell 100, and does not capture any exterior region of the outer shell 100.

Referring to FIG. 5, the outer shell 100 defines a heel opening 250 in an anterior-posterior direction through the leg portion 107 of the outer shell 100. The heel strap 120 and heel pad 170 extend into the heel opening 250. The placement of the heel opening 250 avoids pressure of the patient's heel against the outer shell 100, which is more rigid than the heel pad 170. In some implementations, the patient's heel or padding around the patient's heel may extend into the heel opening 250 when the foot is placed in the boot 20.

The outer shell 100 may be formed of a plastic, such as acrylonitrile butadiene styrene (ABS) or polycarbonate. Other plastics and other materials, such as metal, may additionally or alternatively be used. The cam buckles 50 can be formed of metal or plastic. In some implementations, the cam buckles 50 are formed of steel. The straps 22, 110, 120, 130 can be formed of a fabric mesh or webbing material, for example, a polyester fabric. The straps 22, 110, 120, 130 may alternatively be formed of a flexible band or strip of plastic, metal, or other material. The pads 140, 150, 160, 170, 180, 190 may be formed of a polyester foam, or other foam or padding material.

In some implementations, as shown in FIG. 1, a surgeon places a patient's foot within a disposable padded liner 280 before placing the foot in the boot 20. The padded liner 280 can be formed of a layer of polyester foam or other padding that the surgeon wraps around the foot and leg. The foot can be placed in the boot 20 with the padded liner 280 fastened around the foot. As a result, the padded liner 280 engages the pads 140, 150, 160, 170, 180, 190 within the boot 20 instead of the patient's skin. The additional cushioning of the padded liner 280 can distribute forces to reduce the risk of neurological complications that could be caused by localized pressure on the foot. In addition, the padded liner 280 can be formed of a compressible material that compresses to permit the surgeon to achieve a tighter fitting of the straps 22, 11, 120, 130 around the foot.

Figure 6:
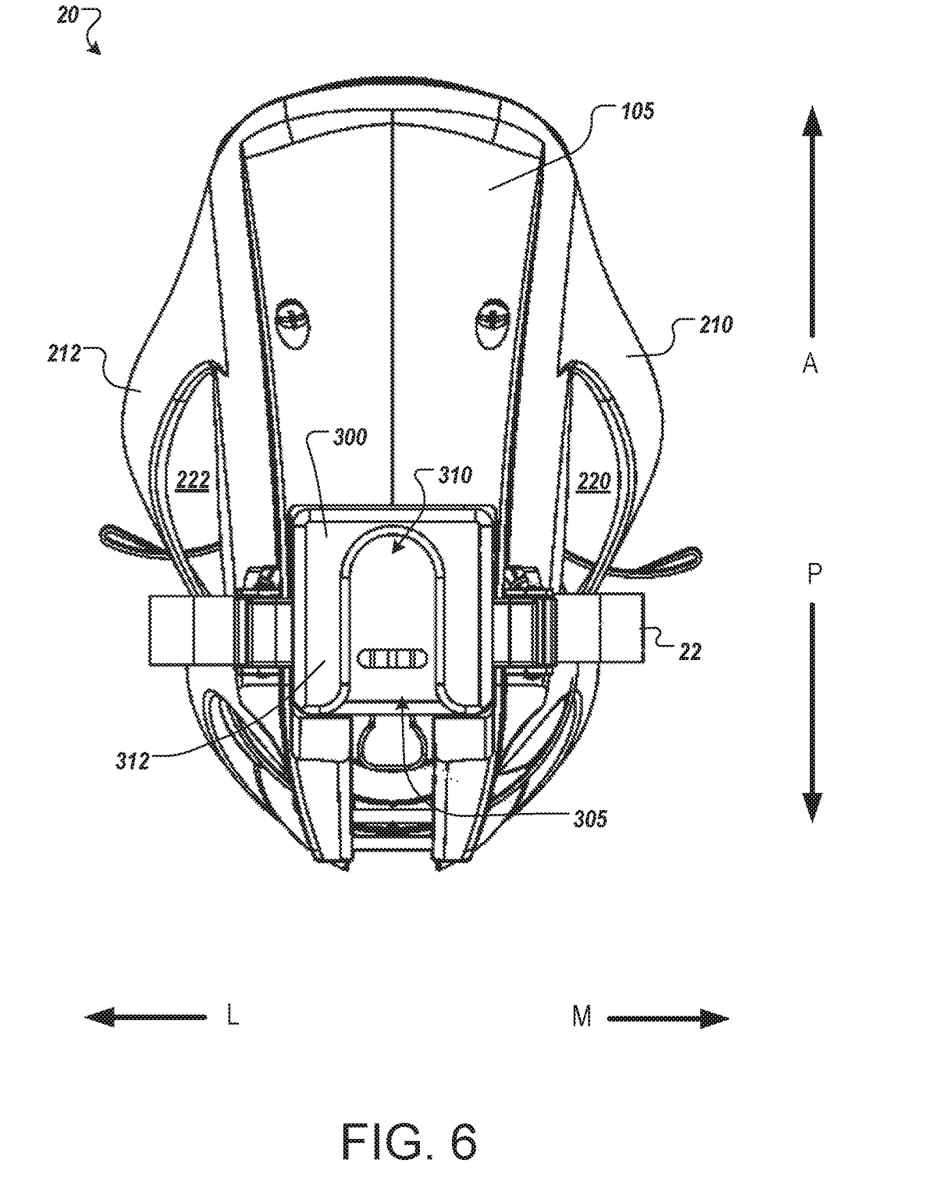
FIG. 6 is a bottom view of the boot.

Referring to FIGS. 5 and 6, the outer shell 100 has a connector 300 for securing the boot 20 to the sliding carriage 40. The connector 300 is mounted to and extends inferiorly from the bottom of the base 105. The connector 300 defines a slot 305 that is oriented generally perpendicular to the superior-inferior axis. The slot 305 is closed on medial, lateral, and anterior sides, but is open at the posterior side to receive a generally planar extension of the sliding carriage 40. The connector 300 also defines a channel 310 extending along the anterior-posterior direction through an inferior side 312 of the connector 300. The channel 310 admits a post of the sliding carriage 40. To connect the boot 20 to the sliding carriage 40, the boot 20 is moved posteriorly so that an extension of the sliding carriage 40 enters the slot 305 and a post of the sliding carriage 40 extends through the channel 310. Within the slot 305, the extension can engage the closed anterior region to limit further travel through the slot 305. A locking mechanism of the sliding carriage 40 can then secure the position of the boot 20 relative to the sliding carriage 40.

Figure 7A:
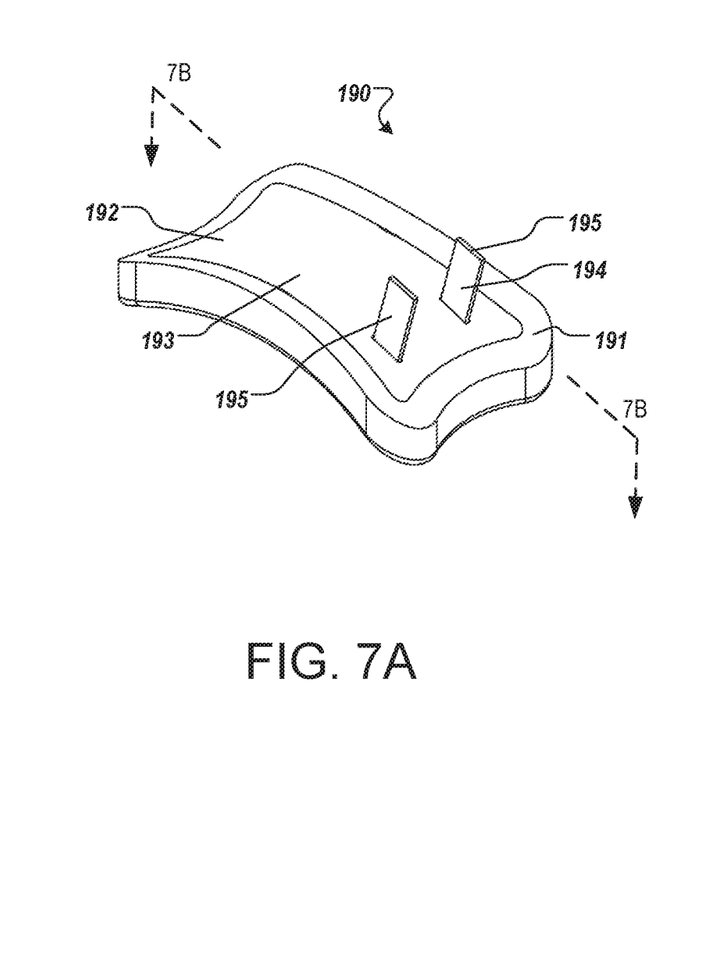
FIG. 7A is a perspective view of a pad of the boot.
Figure 7B:
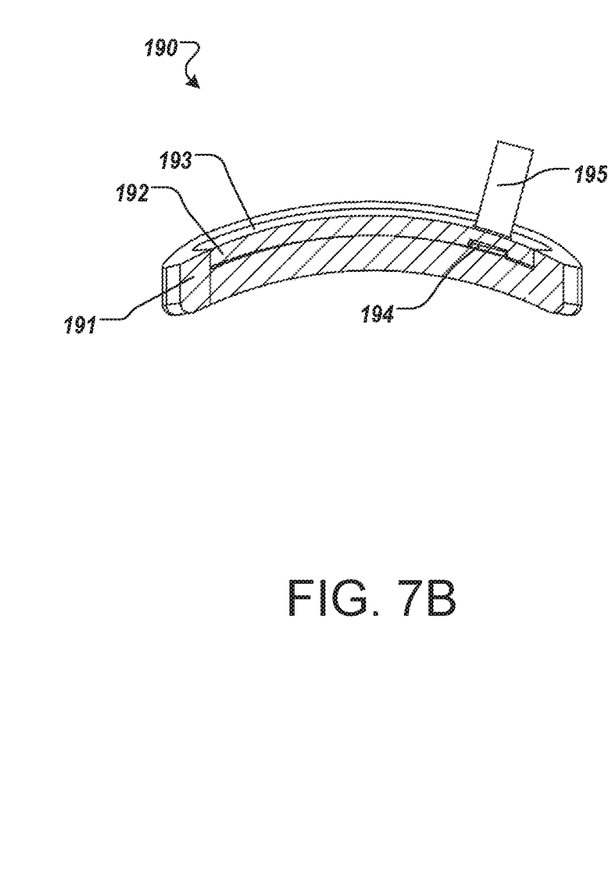
FIG. 7B is a cross-sectional view of the pad along line 7B-7B in FIG. 7A.

Referring to FIGS. 7A and 7B, the bridge pad 190 can include a foam outer portion 191 and a foam inset 192 having an upper surface 193. The bridge pad 190 also includes a flexible band 194 having ends 195 that extend from the upper surface 193. The ends 195 can be wrapped around the retention strap 22 and secured together to capture the bridge pad 190 to the retention strap 22. With the band 194 extending around the strap, the bridge pad 190 may be adjustably positioned by sliding the bridge pad along the length of the retention strap 22. The ends 195 can fasten to each other with Velcro, a buckle, an adhesive, or another fastener.

Figure 8A:
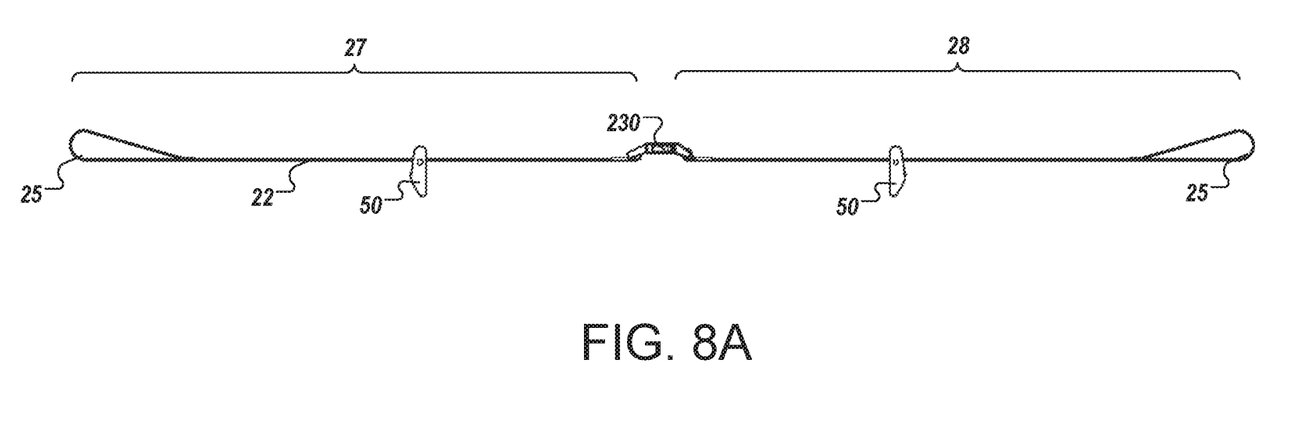
FIG. 8A is a side view of a strap of the boot.
Figure 8B:
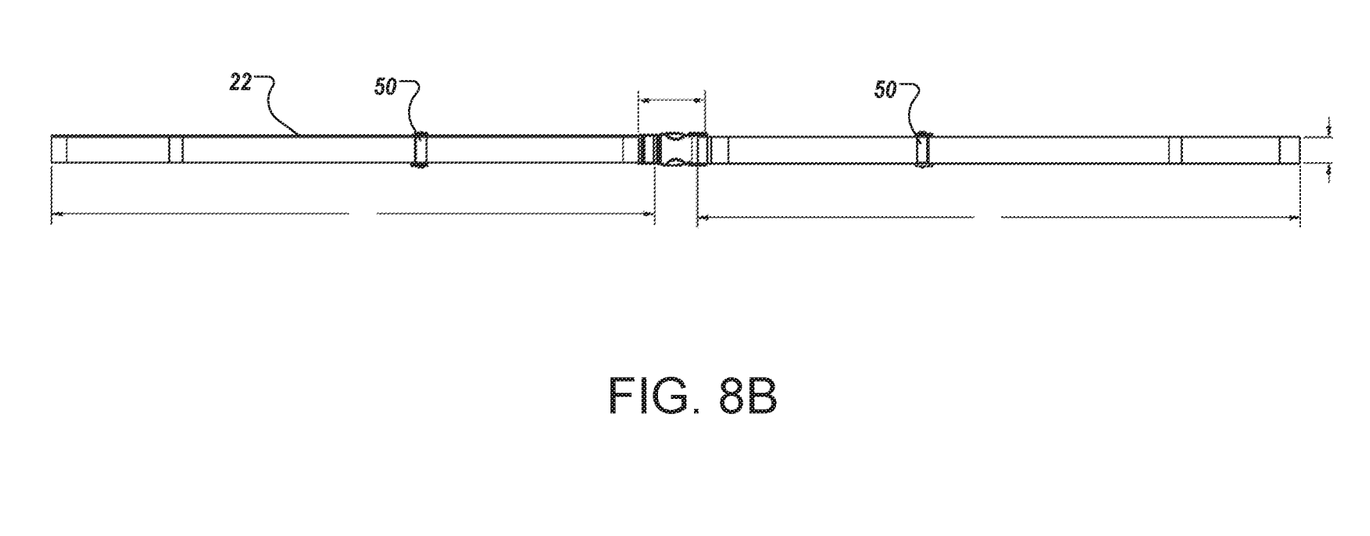
FIG. 8B is a top view of the strap.

Referring to FIGS. 8A and 8B, the retention strap 22 can have ends that form loops 25 that can be used as handles to grasp the retention strap 22. Each loop 25 can have an opening that permits a surgeon to place his fingers through the loop 25, allowing the surgeon to grasp the loop 25 to apply tension to the retention strap 22. The retention strap 22 can have a first portion 27 that extends through a first cam buckle 50, and a second portion 28 that extends through a second cam buckle 50. The buckle 230 connects the two portions 27, 28 in the center of the strap, allowing the two portions 27 to be detached to each other and reattached. Unlike the toe strap 130 and the leg strap 110, the retention strap 22 is not directly attached to the outer shell 100 of the boot. The retention strap 22 is coupled to the boot 20 through engagement with the cam buckles 50, which are fixed to the outer shell 100.

In some implementations, the width, W, of the strap is between approximately 0.5 inches and approximately 2.0 inches, or approximately 1 inch. In some implementations, the length, L, of each portion 27, 28 of the retention strap 22 is between approximately 10 inches and approximately 50 inches, or approximately 24 inches.

In some implementations, alternative fastening mechanisms may be used instead of or in addition to cam buckles. For example, a cleat may be used to provide one-way tensioning of a rope or strap. As another example, a clamp or other mechanism may engage the retention strap 22 to secure the position of the retention strap 22 with respect to the boot 20.

Figure 9:
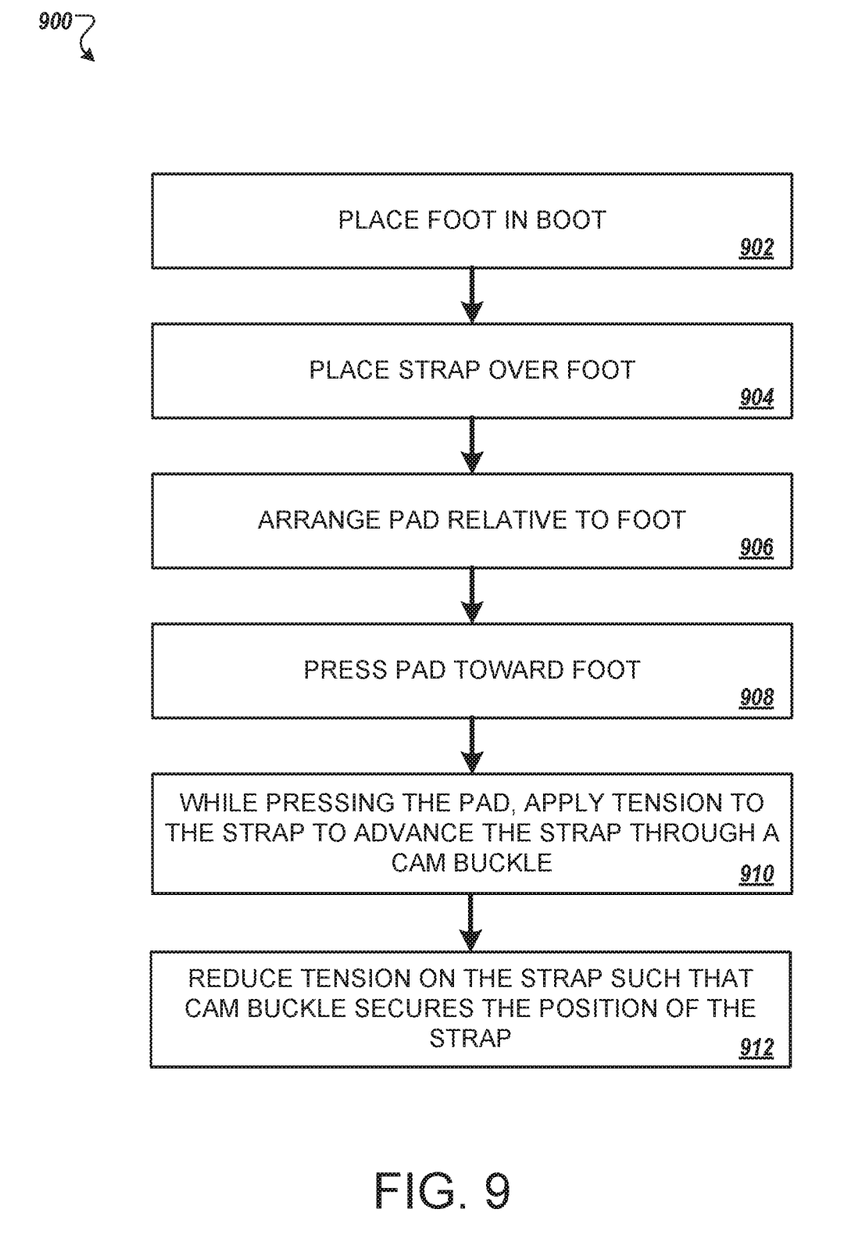
FIG. 9 is a flow diagram of a process for using the boot.
Like reference symbols in the various drawings indicate like elements.

Referring to FIG. 9, a surgeon can use a process 900 to secure a patient's foot in a boot, such as the boot 20. In some implementations, the surgeon places the patient on an operating table, for example, in a supine position, and then secures the foot in the boot. The patient's foot is placed in a boot comprising a cam buckle, a pad, and a retention strap (902). As discussed above, the pad can be a pad that is captured to the retention strap. For example, a portion of the pad can extend around the retention strap to limit removal of the pad from the retention strap while permitting adjustment of the position of the pad along the retention strap.

In some implementations, the patient's foot is placed in a padded liner before the foot is placed in the boot. The padded liner can be a disposable foam liner that wraps around the foot and portions of the leg. The patient's foot and the padded liner wrapped around the foot can be placed in the boot together.

The retention strap is placed over the top of the foot (904). For example, the retention strap may be positioned generally at the ankle, over the bridge or instep of the foot. The retention strap may include two portions that may be connected by a buckle or other fastener. Placing the retention strap over the top of the foot can include connecting the two portions of the retention strap over the top of the foot. As an example, the surgeon can clasp a buckle of the retention strap around the foot, with the buckle being located over the pad and over the top of the foot.

The pad is arranged relative to the top of the foot (906). The pad can be centered between the medial and lateral sides of the foot. In some implementations, the pad is adjustably coupled to the retention strap and located between the retention strap and the top of the foot. For example, the pad may be movable along the length of the retention strap, and to arrange the pad, the pad may be moved along the retention strap to a desired position, for example, between a buckle of the retention strap and the patient's foot.

Pressure is applied to the pad to position the foot within the boot (908). For example, the surgeon can press down on the pad, in a generally inferior direction, to press the foot into the boot. The surgeon can place a hand over the pad, and press the pad with the hand toward the foot and toward a sole of the boot. Pressing on the pad can press the bottom of the foot toward the sole pad of the boot. In addition, pressing on the pad can compress the pad and/or other padding, such as a sole pad under the bottom of the foot or a padded liner around the foot, reducing the amount of force required to advance the retention strap through the cam buckle. A central portion of the retention strap may extend across the pad, and pressing on the central portion of the pad may hold the portion of retention strap extending across the pad in place. The surgeon's hand can also hold the buckle in the center of the retention strap in in place over the patient's foot so advancement of the retention strap does not move buckle from over the top of the foot.

The surgeon may respond to tactile feedback as he advances the retention strap through the cam buckle. For example, while applying tension to an end of the retention strap with one hand, the surgeon may press with his other hand on the pad and a central portion of the retention strap that extends over the pad. With the hand on the pad, the surgeon may detect tension or movement of the central portion of the retention strap. From the tension or movement detected, the surgeon may determine that continued advancement of the retention strap would tend to decenter the retention strap with respect to the foot or over-tighten the retention strap, and the surgeon may reduce tension or release tension on the retention strap in response. Alternatively, the surgeon may determine that tension or movement at the center portion of the retention strap is insufficient, and in response, the surgeon may maintain or increase tension on the end of the retention strap to continue advancing the retention strap through the cam buckle.

While pressure is applied to the pad, tension is applied to the retention strap to advance the retention strap through the cam buckle (910). For example, the surgeon can pull on an end of the retention strap that extends from the boot 20. The surgeon may pull the retention strap in a generally superior direction, for example, in a direction generally parallel to the patient's leg and upward toward the knee. The surgeon may alternatively pull the retention strap in a medial or lateral direction, or in another direction. The retention strap can include a loop at an end, and the surgeon can grasp the end, for example, by placing his fingers or hand through the loop to grasp the end firmly.

The cam buckle can be configured to automatically limit movement of the retention strap through the cam buckle when tension on the retention strap is released. For example, the cam buckle can secure the position of the retention strap without the surgeon needing to manually actuate any control or component of the cam buckle. Thus the cam buckle can be a mechanism that locks the retention strap without user intervention when tension is reduced. The act of reducing or releasing tension on the retention strap may cause the cam buckle to lock the position of the retention strap relative to the boot, without any other user intervention. The cam buckle can allow infinite adjustability of the retention strap relative to the cam buckle by securing the position of the retention strap with respect to the cam buckle at any position along a continuous length of the retention strap.

Maintaining pressure on the pad while advancing the retention strap through the cam buckle may significantly reduce the amount of force needed to advance the retention strap.

In addition, the forces transmitted from the retention strap to the pad can provide tactile feedback to the about the tightness of the retention strap, which can reduce the risk of insufficient tightening or over-tightening.

Tension on the retention strap is reduced to cause the cam buckle to limit movement of the retention strap through the cam buckle (912). The cam buckle can impede the retention strap from receding through the cam buckle (e.g., impeding backward movement of the retention strap opposite the direction the retention strap was advanced through the cam buckle). When the surgeon diminishes tension or releases the retention strap, the cam buckle can engage the retention strap automatically to limit movement of the retention strap through the cam buckle.

In some implementations, the boot includes two cam buckles and the retention strap extends through both cam buckles. Tension can be applied to a first end of the retention strap to advance a first portion of the retention strap through a first cam buckle. Tension can then be applied to a second end of the retention strap to advance a second portion of the retention strap through a second cam buckle. Tension can be applied to the second portion of the retention strap while pressing on the pad. The second cam buckle can be configured to limit movement of the retention strap through the cam buckle when tension on the retention strap (e.g., tension on the second end) is released.

In some implementations, applying tension on the retention strap involves simultaneously tightening a heel strap that extends along a heel of the foot. For example, the heel strap can be looped around the retention strap that is located over the top of the foot. The heel strap can include loops at each end, with the retention strap over the top of the foot passing through each loop. As the retention strap advances through the cam buckle, the retention strap over the top of the foot applies force in an inferior and posterior direction, while the same advancement of the retention strap causes the heel strap to exert a generally anterior force against the back of the foot, for example, at or above the heel of the foot.

In some implementations, the process includes placing a toe strap over toes or forefoot of the foot and tightening the toe strap around the foot. The process can include placing a leg strap around the leg to which the foot is attached and tightening the leg strap around the leg. The toe strap and the leg strap can each include two separate portions coupled to opposite sides of the boot. The two separate portions may be connected around the foot or leg with a buckle or other fastener after the foot is placed in the boot. The toe strap and leg strap may be fastened after the retention strap over the bridge of the foot is tightened, or before.

The boot can be attached to a hip distraction system, and traction can be applied to the patient's leg by applying a force to the boot using the hip distraction system. The boot may be connected to the hip distraction system before or after the foot is placed and secured in the boot. The hip distraction system can also be used to dislocate a hip joint of the patient by applying a force to the boot with the hip distraction system.

The retention strap over the bridge of the foot may be loosened by a surgeon engaging a release mechanism, such as a release button or release lever of the cam buckle, to permit the retention strap to recede through the cam buckle. The release mechanism can be used to reduce pressure on the foot or leg, or to remove the foot from the boot. Some medical procedures may involve temporarily loosening the retention strap during a procedure, and then tightening the retention strap again to complete the procedure.

A number of implementations have been described. Nevertheless, it will be understood that various modifications may be made. Accordingly, other implementations are within the scope of the following claims.

What is claimed is:

1. A boot comprising:
an outer shell having a first side and a second side located opposite the first side;
a first one-way tensioning device coupled to the first side of the outer shell;
a second one-way tensioning device coupled to the second side of the outer shell; and
a strap comprising (i) a first portion having a first handle, and (ii) a second portion having a second handle;
wherein the first one-way tensioning device is configured to engage the first portion of the strap, wherein the first one-way tensioning device is configured to allow movement of the strap in a first direction and to restrain movement of the strap opposite the first direction; and
wherein the second one-way tensioning device is configured to engage the second portion of the strap, wherein the second one-way tensioning device is configured to allow movement of the strap in a second direction and to restrain movement of the strap opposite the second direction.

2. The boot of claim 1, further comprising a buckle configured to join the first portion of the strap and the second portion of the strap.

3. The boot of claim 1, wherein the first handle comprises a first loop of the strap, and the second handle comprises a second loop of the strap.

4. The boot of claim 1, wherein the first handle and the second handle are located outside the outer shell, the first handle and the second handle being located at opposite sides of the outer shell.

5. The boot of claim 1, wherein the first portion of the strap extends through a first opening in the first side of the outer shell, and wherein the second portion of the strap extends through a second opening in the second side of the outer shell.

6. The boot of claim 5, wherein the first portion of the strap extends from the first opening through the first one-way tensioning device to the first handle, and wherein the second portion of the strap extends from the second opening through the second one-way tensioning device to the second handle.

7. The boot of claim 1, wherein the first one-way tensioning device comprises a first cam buckle, and wherein the second one-way tensioning device comprises a second cam buckle.

8. The boot of claim 1, wherein the first one-way tensioning device comprises a cleat or clamp.

9. The boot of claim 1, wherein the first one-way tensioning device has a release mechanism that is configured to allow tension in the strap to be reduced in response to pressure on the release mechanism that is directed toward the boot.

10. The boot of claim 1, wherein the first one-way tensioning device defines a gap that admits a portion of the strap through the first one-way tensioning device; and
wherein the first one-way tensioning device has a release mechanism that is configured to release the strap, the release mechanism being located inferior to the gap.

11. The boot of claim 1, wherein the first portion and the second portion are formed of a fabric mesh or webbing; and
wherein the first handle comprises a first loop of the fabric mesh or webbing that is located at an end of the first portion of the strap, and wherein the second handle comprises a second loop of the fabric mesh or webbing that is located at an end of the second portion of the strap.

12. The boot of claim 1, wherein the outer shell comprises a first handle on the first side, the first one-way tensioning device being located inferior to the first handle of the outer shell; and
wherein the outer shell comprises a second handle of the second side, the second one-way tensioning device being located inferior to the second handle of the outer shell.

13. The boot of claim 1, wherein the strap is a retention strap, and wherein the boot further comprises:
a heel strap having a first portion and a second portion, wherein the first portion of the heel strap is looped around the first portion of the retention strap, and wherein the second portion of the heel strap is looped around the second portion of the retention strap,
wherein the heel strap is configured such that advancing the retention strap through the first one-way tensioning device tightens the heel strap.

14. A boot comprising:
an outer shell having a first side and a second side located opposite the first side;
a first cam buckle coupled to the first side of the outer shell;
a second cam buckle coupled to the second side of the outer shell; and
a strap comprising (i) a first portion having a first handle, and (ii) a second portion having a second handle;
wherein the first cam buckle is configured to allow movement of the strap in a first direction and to restrain movement of the strap opposite the first direction; and
wherein the second cam buckle is configured to allow movement of the strap in a second direction and to restrain movement of the strap opposite the second direction.

15. The boot of claim 14, wherein the first handle comprises a first loop of the strap, and the second handle comprises a second loop of the strap.

16. The boot of claim 14, further comprising a buckle configured to join the first portion of the strap and the second portion of the strap.

17. The boot of claim 16, wherein the first portion and the second portion are formed of a fabric mesh or webbing; and wherein the first handle comprises a first loop of the fabric mesh or webbing that is located at an end of the first portion of the strap, and wherein the second handle comprises a second loop of the fabric mesh or webbing that is located at an end of the second portion of the strap.

18. The boot of claim 14, wherein the first portion of the strap extends through a first opening in the first side of the outer shell, and wherein the second portion of the strap extends through a second opening in the second side of the outer shell.

19. The boot of claim 14, wherein the strap is a retention strap, and wherein the boot further comprises:
   a heel strap having a first portion and a second portion, wherein the first portion of the heel strap is looped around the first portion of the retention strap, and wherein the second portion of the heel strap is looped around the second portion of the retention strap,
   wherein the heel strap is configured such that (i) advancing the retention strap through the first cam buckle tightens the heel strap, and (ii) advancing the retention strap through the second cam buckle tightens the heel strap.

\* \* \* \* \*

UNITED STATES PATENT AND TRADEMARK OFFICE
CERTIFICATE OF CORRECTION

| | | |
|---|---|---|
| PATENT NO. | : 10,575,980 B2 | Page 1 of 1 |
| APPLICATION NO. | : 15/348520 | |
| DATED | : March 3, 2020 | |
| INVENTOR(S) | : John Albert Slusarz, Jr. | |

It is certified that error appears in the above-identified patent and that said Letters Patent is hereby corrected as shown below:

In the Specification

Column 5, Lines 13-24, delete "Referring to FIG. 3B, an example of a cam buckle 50 is shown. One example of a cam buckle that may be used with the boot 20 is part number MCB1, provided by Strapworks.com. The MCB1 cam buckle is a metal cam buckle designed to accept 1" nylon strapping. In some implementations, the cam buckle 50 selected for the boot can be a cam buckle with a load rating of at least 60 pounds of force, or at least 100 pounds of force, or more. In some implementations, the cam buckle 50 may be designed to operate with applied forces of at least 250 pounds, at least 500 pounds, at least 750 pounds, or more." and insert the same at Column 5, Line 14 as a new paragraph.

Column 7, Lines 31-39, delete "When the retention strap 22 is tightened, the patient's ankle exerts an anterior force on the retention strap 22, which is out of alignment with the cam buckle 50. The heel strap 120 engages the patient's heel and pulls posteriorly on the portions of the retention strap 22 passing through the loops 122, which can align the retention strap 22 with the cam buckle 50 by counteracting some or all of the anterior force exerted on the retention strap 22 by the top of the patient's foot." and insert the same at Column 7, Line 31 as a continuation of the same paragraph.

Column 10, Lines 58-64, delete "The patient's foot is placed in a boot comprising a cam buckle, a pad, and a retention strap (902). As discussed above, the pad can be a pad that is captured to the retention strap. For example, a portion of the pad can extend around the retention strap to limit removal of the pad from the retention strap while permitting adjustment of the position of the pad along the retention strap." and insert the same at Column 10, Line 61 as a new paragraph.

Column 12, Lines 23-26, delete "In addition, the forces transmitted from the retention strap to the pad can provide tactile feedback to the about the tightness of the retention strap, which can reduce the risk of insufficient tightening or over-tightening." and insert the same at Column 12, Line 22 as a continuation of the same paragraph.

Signed and Sealed this
Twelfth Day of May, 2020

Andrei Iancu
*Director of the United States Patent and Trademark Office*